United States Patent [19]

Ratcliffe et al.

[11] 4,387,247

[45] Jun. 7, 1983

[54] CATALYTIC REDUCTION OF NITRO AROMATIC COMPOUNDS WITH HYDROGEN SULFIDE AND CARBON MONOXIDE

[75] Inventors: Charles T. Ratcliffe; Geza Pap, both of Morristown, N.J.

[73] Assignee: Allied Corporation, Morris Township, Morris County, N.J.

[21] Appl. No.: 158,552

[22] Filed: Jun. 11, 1980

[51] Int. Cl.³ .............................................. C07C 85/11
[52] U.S. Cl. .................................... 564/420; 564/413; 564/421; 564/422; 564/163; 564/166; 564/167; 564/170; 564/171; 564/172; 564/180; 546/1; 546/152; 252/411 S
[58] Field of Search ............... 564/413, 420, 421, 422; 546/152, 1; 252/411 S

[56] References Cited

U.S. PATENT DOCUMENTS

| | | | |
|---|---|---|---|
| 1,237,828 | 8/1917 | Schmidt et al. | 564/420 X |
| 2,402,439 | 6/1946 | Owen | 564/421 |
| 2,455,713 | 12/1948 | Voorhies | 564/421 X |
| 2,620,356 | 12/1952 | Munday | 564/421 |
| 3,637,820 | 1/1972 | Dodman et al. | 564/420 X |
| 3,739,026 | 6/1973 | Wilson | 564/422 X |
| 3,801,640 | 4/1974 | Knifton | 564/422 X |
| 3,935,264 | 1/1976 | Bhutani | 564/422 |
| 4,079,072 | 3/1978 | Finch | 252/411 S X |

*Primary Examiner*—Paul F. Shaver
*Attorney, Agent, or Firm*—Kenneth E. Stroup, Jr.; Alan M. Doernberg; Gerhard H. Fuchs

[57] ABSTRACT

In the reduction of di- or polynitro aromatic compounds by gaseous $H_2S$ over a solid catalyst, addition of CO gas promotes formation of amino groups from all nitro groups in the molecule. A preferred embodiment is reduction of 2,4- and/or 2,6-dinitrotoluene in vapor phase at 325° C. over a supported iron or supported cobalt catalyst on a support comprising alumina. The amino products are useful for production of polyurethane resins.

20 Claims, No Drawings

CATALYTIC REDUCTION OF NITRO AROMATIC COMPOUNDS WITH HYDROGEN SULFIDE AND CARBON MONOXIDE

FIELD OF THE INVENTION

This invention relates to a process for reducing di- and polynitro aromatic compounds to corresponding aromatic amines.

BACKGROUND OF THE INVENTION

Conventional reduction of dinitro aromatic compounds to aromatic diamines is practiced with hydrogen as a reducing agent and noble metal catalysts. Large amounts of hydrogen are consumed in the process and the noble metal catalysts are expensive.

D. M. Gold in U.S. Pat. No. 3,255,252 issued June 7, 1966 discloses reacting hydrogen sulfide and organic mono- and dinitro compounds in liquid phase (see col. 3, line 54) to form amines. Specifically in the working example, nitro benzene, in a heated autoclave under pressure is reacted with hydrogen sulfide in the presence of a silica/alumina catalyst to form aniline. Other heterogeneous catalysts disclosed but not exemplified in quantitative examples are associations of silica and various amphoteric metal oxides and particularly those of alumina, thoria and zirconia, e.g., active clay, synthetic alumina-silica, thoria-silica and zirconia-silica catalysts. It is stated that related conversion "can be realized," e.g., "nitrotoluenes" to "nitrotoluidenes, toluene diamines," but no quantitative examples are given.

J. J. Wise in U.S. Pat. No. 3,253,038 issued 1968 similarly discloses reduction of specifically only nitrobenzene, with hydrogen sulfide, preferably in the vapor phase at 300° C. over a crystalline alumina zeolite as catalyst (especially in the sodium form). It is indicated that in aromatic compounds containing two or more nitro groups, one of these can be selectively reduced by the subject process.

G. E. Etzel in J. Phys. Chem. Vol. 32 page 852 describes investigations relating to the catalytic activity of titania in the reduction of nitro compounds with hydrogen, and cites earlier studies using catalysts such as iron, cobalt, alumina, and numerous others.

Murata in Organic Chemistry (Japan) Volume 35, 61 (1977) discloses the reduction of aromatic nitro compounds with hydrogen sulfide in liquid phase.

The prior art might suggest, and we have confirmed, that when gaseous hydrogen sulfide is employed as the reducing agent for catalytic reduction of dinitroaromatics, the proportion of diamine in the resulting product is low. Moreover, we have ascertained that using catalysts representative of known reduction catalysts, the activity observed for diamine production declines rapidly.

We have now found conditions under which hydrogen sulfide is effective for reduction of two or more nitro groups in di- and/or poly nitroaromatics to amino groups and remains so for extended periods of running.

SUMMARY OF THE INVENTION

Our improvement consists essentially in providing in the heterogeneous catalytic reduction of a di- or polynitroaromatic compound by gaseous hydrogen sulfide over a solid catalyst, an effective proportion of carbon monoxide gas together with the hydrogen sulfide, thereby obtaining reduction of two or more nitro groups in said compound to afford di- or polyamines as the major reaction products. By "an effective proportion" of carbon dioxide we mean that the proportion is, as we have observed, sufficient at least to prolong materially the life of the catalyst, for reduction of at least two nitro groups in the aromatic compound to amino groups. The solid catalyst preferably contains at least one transition element as a component. Although we do not wish to be bound by any theory, we believe that carbon monoxide is effective in this reaction by reacting with sulfur deposited on the catalyst to form carbonyl sulfide. Carbon monoxide also reacts with certain of the transition metal catalysts to form intermediate carbonyl complexes which regenerate the active phase of the catalyst.

DETAILED DESCRIPTION OF THE PREFERRED EMBODIMENTS

Di- or polynitroaromatic compounds are reduced to di- or polyaminoaromatic compounds with a mixture of hydrogen sulfide and carbon monoxide in the presence of a solid catalyst, preferably as outlined below, in accordance with this invention.

STARTING AROMATIC NITRO COMPOUNDS

The di- or polynitro compounds useful in the present invention for conversion to corresponding amines have the general formula $$Ar(NO_2)_i X_k H_n$$

wherein
- Ar is an aromatic ring system comprising carbon and/or nitrogen
- i is at least 2;
- X is a substituent group, such as hydroxy, alkanoyl, alkoxy, carboxy, carboxyalkyl ester, alkyl, cycloalkyl, aryl, amino, substituted amino;
- k is from 0 to 4
- H is hydrogen
- n corresponds to the number of bonds of the ring system not occupied by a nitro group or by an X group, such that k and n together satisfy the remaining valances of the nitroaromatic compound.

More particularly in these compounds; Ar is
- an aromatic $C_6$ ring,
- an aromatic $C_{10}$ double ring system;
- an aromatic $C_5N$ ring; or
- an aromatic $C_9N$ double ring system; and when k is at least equal to 1, independently X is:
$C_1$–$C_{20}$ alkyl, $C_1$–$C_{20}$ alkanoyl, $C_1$–$C_{20}$ alkoxy, cycloalkyl, or noncondensed aromatic ring bound via a carbon atom, or two X's together form a condensed aromatic ring system or form an aliphatic ring; and wherein one or more of the hydrogen atoms of X can be independently substituted by amino, alkylamino, nitrilo, hydroxy, carboxy, $C_1$–$C_5$ alkyl, $C_1$–$C_5$ alkoxy, $C_1$–$C_5$ alkanoyl, up to $C_{12}$ aryl and up to $C_{12}$ cycloalkyl groups.

Preferred dinitro compounds for use in the present invention have the formula $$Ar(NO_2)_2 R_4$$

wherein Ar is a $C_6$ benzene ring, and wherein R is independently hydrogen, $C_1$–$C_{10}$ alkyl, phenyl, pyridyl, biphenyl, benzyl, naphthyl, amino, $C_1$–$C_{10}$ alkylamino, nitrilo, hydroxy, carboxyl, $C_1$–$C_5$ alkanoyl or $C_1$–$C_5$ alkoxy.

Exemplary dinitro aromatic compounds include meta- and para- dinitrobenzene,
2,4-dinitrophenol,
2,4-dinitrotoluene
2,6-dinitrotoluene
2,4-dinitro-1-naphthol,
2,4-dinitroethylaniline
2,3-dinitro-toluene
3,4-dinitro-1,2-dimethylbenzene
2,3-dinitrophenyl alkyl ether
2,3-dinitro-1-methyl-4-methylaminobenzene
5,6-dinitro-1,2,4-trimethoxybenzene
1,2-dinitronaphthalene
2,3-dinitronaphthalene
dinitrodiacetoxyphenanthrene
dinitrodibenzylsulfide Polynitroaromatic compounds preferred for use in the present invention have the formula $$Ar(NO_2)_m R_n$$

wherein Ar is
an aromatic $C_6$ ring;
an aromatic $C_{10}$ double ring system;
an aromatic $C_5N$ ring; or
an aromatic $C_9N$ double ring system;
wherein
m is 3, 4 or 5 for a $C_6$ ring or a $C_5N$ ring; and
m is 3, 4, 5, 6, or 7 for a $C_{10}$ double ring or for a $C_9N$ double ring system; and wherein
independently R is hydrogen, $C_1$-$C_{20}$ alkyl, $C_1$-$C_{20}$ alkanoyl, $C_1$-$C_{20}$ alkoxy, or noncondensed aromatic ring bound via a carbon atom; or two R's together form a condensed aromatic ring or form an aliphatic ring; and wherein one or more of the hydrogen atoms of R can be independently substituted by amino, alkylamino, nitrilo, hydroxy, carboxy, $C_1$-$C_5$ alkyl, carboxy, $C_1$-$C_5$ alkoxy, up to $C_{12}$ aryl and up to $C_{12}$ alkanoyl groups.

Such polynitroaromatic compounds are, more particularly, trinitro derivatives of benzene, toluene, phenol, resorcinol or naphthalene, with the nitrogroups non-vicinal, especially
2,4,6-trinitrotoluene
2,4,6-trinitroresorcinol
1,3,5-trinitrobenzene
picric acid (i.e. 2,4,6-trinitrophenol)

Our invention can be carried out with the nitroaromatic compound being in the liquid phase or in the vapor phase. When in the liquid phase, the di- or polynitro aromatic compound is preferably dissolved in an inert organic solvent, such as o-xylene, toluene, dichlorobenzene, or acetic acid. The solvent is desirable to reduce any tar formation. However, use of sufficient proportions of carbon monoxide in accordance with our invention is found to practically eliminate the problem of tar formation when the reaction is carried out under vapor phase conditions.

CATALYSTS

The solid catalysts of the present invention include catalysts useful in the conventional reduction of nitro aromatic compounds with hydrogen or hydrogen sulfide. Preferred catalysts include compositions containing transition metal compounds, especially those of metals in the first transition series of Group VIII.

Preferred catalysts are supported catalysts having a surface containing at least one such Group VIII metal component especially iron or cobalt, such catalysts supported on a catalyst support comprising alumina, especially the gamma form of alumina. The activity of these catalysts appears to be associated with the presence of metal as a sulfide such as $Co_3S_4$ on the surface of the catalysts. Carbon monoxide is believed to aid in maintaining this phase in the presence of hydrogen sulfide. The catalyst should be a sulfur active catalyst.

Sulfur active catalysts are materials which upon being sulfided have catalytic properties in hydrodesulfurization reactions. Such catalysts are described by Otto Weiser and Stanilav Landa in: "Sulfur Catalysts, Their Properties and Applications," Pergamon Press, Oxford and New York (1973). Such sulfur-active catalysts include compositions comprising nickel, tungsten, cobalt, iron, ruthenium, rhodium, iridium, copper, molybdenum, chromium in supported and non-supported state. Such catalysts can be employed as a precursor which is deposited on the support material and then transformed into an active state which is generally a sulfide. High surface area supports such as gamma alumina, $SiO_2$, $TiO_2$ or active carbon can be used.

Preferably the catalysts are presulfidized.

We have found that preferred loadings of metal on the support are usually in the range of 2-10%; and that catalysts having higher loadings of cobalt and other metals can be less effective than catalysts with 2-10% loading.

REACTION CONDITIONS

The mole ratio of CO to $H_2S$ in the feed gas mixture can range from about 1:20 to about 20:1; but the concentrations of carbon monoxide should be kept high enough to be effective in avoiding rapid decay of the catalyst activity. A preferred range is from about 1:2 to about 2:1 of CO:$H_2S$ in the feed gas.

A mixture of hydrogen sulfide and carbon monoxide is a potential waste gas from coal cleaning and coal gasification, which could be employed in the present reaction as such.

The ratio of the reducing gas to the nitro compound should be of about a stoichiometric amount or greater based on the following equation for each nitro group:

$$3H_2S + 3CO + ArNO_2 \rightarrow ArNH_2 + 2H_2O + 3COS$$

This equation is only a gross or overall equation, since there are various equilibria involved in the gas phase under reaction conditions.

The hydrogen sulfide/carbon monoxide gas mixture is preferably employed under pressure. The reaction pressure is not critical and a range from about 1 kPa to 5,000 kPa is preferred. More preferred is a pressure range from about 200 to 2000 kPa. However, higher pressures will enhance the rate of reaction although they are more cumbersome to handle.

The reaction temperature can range from about 100° C. to 500° C. and is preferably from about 270° C. to 350° C.

CONCURRENT ALKYLATION AND DEALKYLATION REACTION

In the presence of certain catalysts an intermolecular exchange of the methyl group in the aromatic ring occurs:

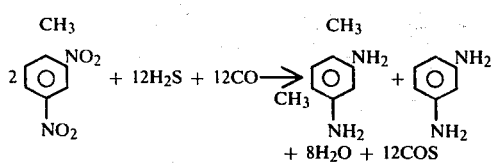

Catalysts inducing this exchange reaction include nickel-containing catalysts.

Catalysts suppressing this exchange reaction include iron and cobalt catalysts.

CONCURRENT METHYLATION REACTION

It was found that certain very active catalysts induce methylation concurrent with the reduction of nitroaromatic compounds.

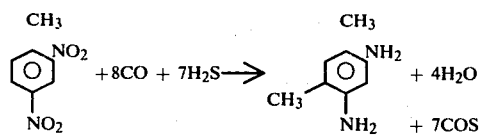

Similarly di- and polymethylation can be performed.

Base-treated Co-Mo catalysts are most active for this reaction. We have observed as secondary products, especially when using these catalysts, considerable formation of benzothiazoles, apparently resulting from reaction of carbon oxysulfide and/or carbon disulfide with amino groups.

APPARATUS

The reaction vessel for the present invention is preferably of such a material which is resistant to hydrogen sulfide, carbon monoxide, water and their mixtures. Materials and linings for such vessels include polytetrafluoroethylene, glass, and Inconel nickel/chromium alloy.

The reaction of this invention preferably employs a continuous flow of hydrogen sulfide and carbon monoxide into the system and removal of product gases and water as vapors during the reaction. A countercurrent flow of hydrogen sulfide/carbon monoxide mixture and of di or polynitro aromatic compound can be employed followed by removal of the resulting amine on the hydrogen sulfide/carbon monoxide mixture input side and removal of the gases and water on the di- or polynitro aromatic compound input side. Alternatively, a back mix reactor can be advantageously used to carry out the reaction.

PRODUCTS

The gas phase reduction of di- and polynitro aromatic compounds with hydrogen sulfide and carbon monoxide provides full reduction of di- or polynitro aromatic compounds to the corresponding di- or polyamino aromatic compounds under proper catalyst and reaction conditions.

PREFERRED EMBODIMENT 2,4-dinitrotoluene and/or 2,6-dinitrotoluene is contacted in the vapor phase with a 1:1 mole ratio mixture of hydrogen sulfide and carbon monoxide at 325° C. over an iron catalyst or a cobalt catalyst on an alumina or silica/alumina support. The contact time is approximately 0.3 second.

EXAMPLES

A microcatalytic flow reactor with a fixed level of 1.35 grams of catalyst was employed.

A concurrent flow of hydrogen sulfide, carbon monoxide, dinitrotoluene in toluene and nitrogen gas was passed through a vertical reactor tube into a preheated chamber containing quartz chips. The preheated chamber was located directly above the catalyst bed, and the flow passed from the preheated chamber to the catalyst bed.

Liquid products from the reaction were trapped in collection bottles located in a lower collection tube, which was cooled with ice. Gas chromatographic analysis of the liquid samples was carried out on a 3 percent silicone oil on Chromosorb W column.

Chromatographic columns were employed to separate all components for identification by their chemical ionization mass spectra. Gas phase samples from the inlet and exit stream were also analyzed with gas chromatography.

The catalysts employed in the Examples were either obtained commercially or prepared by conventional methods.

The catalysts of Table 1, runs #85-45 and #85-46 were prepared by depositing a cobalt nitrate solution on $Al_2O_3$ (Harshaw 0104), drying the resulting composite in air to decompose the nitrate to the oxide and then this was presulfidized by heating in hydrogen sulfide.

The catalysts of Table I, runs #85-41 and 85-40 were obtained by depositing rhodium on alumina and carbon, respectively, followed by sulfidation.

The catalyst of Table I, run #85-36 was made by depositing ammonium molybdate on aluminum oxide, followed by deposition of cobalt nitrate and heating and sulfidation. After sulfidation this catalytic composition comprises molybdenum disulfide and cobalt sulfides (9% as Mo, 3% as Co, by wgt.)

The catalyst of Table I run #34-10 was very similar to that of run #85-36, except that the alumina was obtained from a different source.

The catalyst designations in Table I list first the weight percentage of the activator (if any) of the formula given in the catalyst composition and then the support material. Source indications are given in brackets.

The results of a number of exemplary reactions are set forth in Table 1. As can be seen from most of the examples, the catalyst degrades with time resulting in a decrease of the yield of diamino products with time. However as seen in Example 7, the catalyst activity for amino products can be at least partially regenerated by contact with a stream of hydrogen at 400° C.

TABLE I

Gas Phase Reduction of 2,4-Dinitrotoluene with $H_2S/CO$

Reaction Temperature = 325° C.
Contact Time = 0.5 seconds
Inlet Mixture (mmoles/hour):
  2,4-Dinitrotoluene = 1.1
  $N_2$ = 54.0
  Toluene (Solvent) = 10.8
  CO = 80.0
  $H_2S$ = 80.0

PART A

| Ex. # | Catalyst | Run # | Sample Time (min) |
|---|---|---|---|
| 1 | 10% $Fe_2O_3$ on $Al_2O_3$ (Harshaw 0104 | 40-28 | 104 200 |

TABLE I-continued
Gas Phase Reduction of 2,4-Dinitrotoluene with H₂S/CO

| | | | |
|---|---|---|---|
| | Support) | | 755 |
| | | | 1050 |
| | | | 1400 |
| 2 | 10% NaOH on Fe 0301 | 40-17 | 51 |
| | (Harshaw 20% Fe₂O₃ on | | 360 |
| | Al₂O₃) | | 500 |
| | | | 700 |
| 3 | 10% Fe₂O₃ on | 40-34 | 90 |
| | Al₂O₃ (Girdler T-1746 | | 200 |
| | Support) | | 450 |
| | | | 700 |
| 4 | 5% MoO₃ on | 59-11 | 120 |
| | Al₂O₃ (Girdler T-1746 | | 240 |
| | Support) | | 360 |
| 5 | Ni 3210 | 85-21 | 52 |
| | (Harshaw 35% Ni on | | 200 |
| | Si/Al₂O₃) | | 360 |
| 6 | Co 1506 (Harshaw | 52-40 | 102 |
| | 35% Co on SiO₂/Al₂O₃) | | 300 |
| | | | 600 |
| 7 | Run 52-40 Catalyst, | 34-19 | 32 |
| | Regenerated, H₂, 400° C., | | 60 |
| | then cooled to 325° C. | | |
| 8 | 5% Co on Al₂O₃ | 85-45 | 35 |
| | (Harshaw 0104) | | 270 |
| | | | 400 |
| | | | 715 |
| | | | 1020 |
| 9 | 30% Co on Al₂O₃ | 85-46 | 81 |
| | (Harshaw 0104) | | 210 |
| | | | 360 |
| 10 | Al₂O₃ | 85-43 | 34 |
| | (Harshaw 0104) | | 160 |
| | | | 280 |
| | | | 800 |
| 11 | 5% Pd on Al₂O₃ | 85-41 | 47 |
| | | | 120 |
| | | | 500 |
| 12 | 5% Pd on C | 85-40 | 90 |
| | | | 321 |
| 13 | TiO₂ | 22-15 | 54 |
| | | | 200 |
| | | | 312 |
| | Use of Co—Mo Catalysts | | |
| 14 | 3% Co, 9% Mo on Al₂O₃ | 85-36 | 180 |
| | XL-649A (Davidson); | | 310 |
| 15 | 3% Co, 9% Mo on Al₂O₃ | 34-10 | 51 |
| | (HT-400E Harshaw) + 10% | | 120 |
| | K₂CO₃ | | |

PART B
(Product Distribution (Mole %) - See Footnote

| Ex. # | DAB | DAT | MeDAT | 4A2NT | 2A4NT | DNT |
|---|---|---|---|---|---|---|
| 1 | 9.3 | 61.0 | 29.6 | — | — | — |
| | — | 100.0 | — | — | — | — |
| | — | 100.0 | — | — | — | — |
| | — | 94.8 | — | 5.12 | — | — |
| | — | 83.76 | — | 7.7 | 5.3 | 3.29 |
| 2 | — | 100.0 | — | — | — | — |
| | — | 85.9 | — | 14.1 | — | — |
| | — | 85.9 | — | 38.6 | 5.4 | — |
| | — | 30.8 | — | 49.1 | 16.3 | 3.6 |
| 3 | 8.54 | 63.2 | 28.2 | — | — | — |
| | — | 100.0 | — | — | — | — |
| | — | 100.0 | — | — | — | — |
| | — | 93.3 | — | 3.7 | — | — |
| 4 | 5.2 | 68.8 | 26.0 | — | — | 17.2 |
| | — | 21.5 | — | 38.7 | 22.6 | 32.6 |
| | — | 5.7 | — | 37.4 | 24.1 | — |
| 5 | 27.4 | 55.9 | 16.6 | — | — | — |
| | 10.5 | 67.6 | 21.7 | — | — | — |
| | 8.5 | 55.3 | 12.3 | 15.2 | 5.6 | 2.17 |
| 6 | — | 83.9 | 6.0 | 10.5 | trace | — |
| | — | 17.6 | — | 32.1 | 19.2 | 31.1 |
| | — | 12.4 | — | 34.5 | 18.8 | 34.2 |
| 7 | 6.25 | 66.5 | — | 15.5 | 6.3 | 5.3 |
| | 3.1 | 59.3 | — | 22.1 | 9.3 | 6.2 |
| 8 | 13.5 | 50.9 | 35.5 | — | — | — |
| | 4.5 | 70.0 | 25.5 | — | — | — |
| | 5.2 | 76.3 | 18.4 | — | — | — |
| | 5.8 | 81.1 | 13.1 | — | — | — |
| | 4.6 | 80.2 | 9.5 | 5.2 | — | — |
| 9 | 5.4 | 55.3 | 38.1 | — | — | — |
| | 5.1 | 70.0 | 15.4 | 9.4 | — | — |
| | 2.0 | 57.0 | — | 29.2 | 10.6 | — |
| 10 | 13.9 | 86.0 | — | — | — | — |
| | 11.9 | 80.3 | — | 8.1 | — | — |
| | 3.9 | 35.5 | — | 50.2 | 9.6 | — |
| | — | 5.4 | — | 40.5 | 27.4 | 26.5 |
| 11 | 15.9 | 71.4 | 12.6 | — | — | — |
| | 2.3 | 23.3 | — | 47.8 | 16.9 | 9.7 |
| | — | 4.12 | — | 42.6 | 27.9 | 25.3 |
| 12 | 40.1 | 52.1 | 7.8 | — | — | — |
| | 4.9 | 21.1 | — | 43.8 | 21.6 | 8.5 |
| | 3.9 | 70.1 | 25.9 | — | — | — |
| | 6.1 | 65.4 | 28.6 | — | — | — |
| | 2.2 | 78.5 | 19.3 | — | — | — |
| | 11.1 | 39.4 | 26.3 | — | — | 9.75[c] |
| | 11.4 | 56.8 | 28.6 | — | — | 3.2[c] |
| | 15.2[a] | 10.0 | 29.3 | 17.3[b] | — | 27.3[c] |
| | 7.4 | 30.9 | 28.1 | 7.3[b] | — | 23.6[c] |
| | 2.7[a] | | | | | |

Footnote:
DAB = meta-diaminobenzene
DAT = 2,4-diaminotoluene
MeDAT = 5-methyl-2,4-diaminotoluene
4A2NT = 4-amino-2-nitrotoluene
2A4NT = 2-amino-4-nitrotoluene
DNT = 2,4-dinitrotoluene
[a]aminotoluene
[b]dimethyldiaminotoluene
[c]benzothiazole products

We claim:

1. In a process for the heterogeneous catalytic reduction of di- or polynitro aromatic compounds by gaseous hydrogen sulfide over a solid catalyst, the improvement which comprises adding to the hydrogen sulfide gas an amount of carbon monoxide effective to prolong the life of the catalyst for catalytic reduction of at least two nitro groups to amino groups.

2. The process according to claim 1 wherein the solid catalyst contains at least one transition element as a component.

3. The process according to claim 2 wherein the aromatic di- or polynitro compound has a composition of the formula $$Ar(NO_2)_i X_k H_n$$

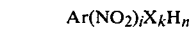

wherein Ar is
 an aromatic $C_6$ ring,
 an aromatic $C_{10}$ double ring system,
 an aromatic $C_5N$ ring, or
 an aromatic $C_9N$ double ring system; and
wherein i is at least 2; and
wherein X is a substituent group as defined below; and
wherein k is from 0 to 4; and
wherein k and n together satisfy the remaining valences of the nitroaromatic compound; and
when k is at least 1, independently X is: $C_1$–$C_{20}$ alkyl, $C_1$–$C_{20}$ alkanoyl, $C_1$–$C_{20}$ alkoxy, cycloalkyl, or noncondensed aromatic ring bound via a carbon atom; or two X's together form a condensed aromtic ring system or form an aliphatic ring;
and wherein one or more of the hydrogen atoms of "X" can be independently substituted by amino, alkylamino, nitrilo, hydroxy, carboxy, $C_1$–$C_5$ alkyl, $C_1$–$C_5$ alkoxy, $C_1$–$C_5$ alkanoyl, up to $C_{12}$ aryl and up to $C_{12}$ cycloalkyl groups.

4. The process according to claim 2 wherein the aromatic compound has the formula Ar $(NO_2)_2$ $R_4$ wherein Ar is a benzene ring, and wherein R is independently hydrogen, $C_1$-$C_{10}$ alkyl, phenyl, pyridyl, biphenyl, benzyl, naphthyl, amino, $C_1$-$C_{10}$ alkylamino, nitrilo, hydroxy, carboxyl, $C_1$-$C_5$ alkanoyl, or $C_1$-$C_5$ alkoxy.

5. The process according to claim 2 wherein the solid catalyst is a sulfur active catalyst and contains at least one Group VIII transition metal component.

6. The process according to claim 5 wherein the catalyst is a supported iron-containing catalyst.

7. The process according to claim 5 wherein the catalyst is a supported cobalt-containing catalyst.

8. The process according to claim 5 wherein the catalyst is a supported iron- or cobalt-containing catalyst, on a support comprising alumina.

9. The process according to claim 5 wherein the nitro compound is meta- or para- dinitrobenzene.

10. The process according to claim 5 wherein the nitro compound is meta- or para- dinitrotoluene.

11. The process according to claim 5 wherein the nitro compound is a trinitro derivative of benzene, toluene, phenol, resorcinol or naphthalene, with the nitro groups non-vicinal.

12. The process according to claim 1 wherein the reaction temperature is from about 100° C. to 500° C.

13. The process according to claim 12 wherein the pressure of the CO/$H_2$S gas mixture is in the range from about 1 to about 5,000 kPa.

14. The process according to claim 13 wherein the aromatic compound is in the vapor phase and the reaction temperature is from about 270° C. to 350° C. and the catalyst is a sulfur active catalyst containing at least one Group VIII transition metal component of a metal in the first transition series.

15. The process according to claim 14 wherein the mole ratio of CO:$H_2$S in the feed gas is in the range from about 1:20 to about 20:1.

16. The process according to claim 15 wherein said mole ratio is from 1:2 to 2:1 and the pressure of the said gas mixture is from about 200 to 2,000 kPa.

17. The process as set forth in claim 1 wherein the di- or polynitro aromatic compound is an alkylated aromatic system and wherein a reaction time is provided sufficient to induce concurrent alkyl group exchange between different aromatic rings under the reaction conditions.

18. The process according to claim 17 wherein a base treated cobalt-molybdenum catalyst is employed.

19. The process according to claim 1 wherein said solid catalyst is of the type for which the proportion of di- and polyamine reaction products is low.

20. The process according to claim 1 wherein said catalyst is of the type which is deactivated or poisoned by the deposition of elemental sulfur.

* * * * *